United States Patent
Ademovic et al.

(10) Patent No.: US 7,544,653 B2
(45) Date of Patent: Jun. 9, 2009

(54) ADDITIVE CYTOPROTECTIVE EFFECTS OF TWO BIOACTIVE REGIONS OF PRO-OPIOMELANOCORTIN HORMONE

(76) Inventors: Zlatko Ademovic, Titova 17, 76290 Odzak (BA); Nikola Stambuk, Subiceva 16, 10 000 Zagreb (HR); Pasko Konjevoda, Stjepana Draganica 1, 10 000, Zagreb (HR); Darko Mikus, Kukuljeviceva 10, 21 000, Split (HR)

( * ) Notice: Subject to any disclaimer, the term of this patent is extended or adjusted under 35 U.S.C. 154(b) by 0 days.

(21) Appl. No.: 10/492,908

(22) PCT Filed: Nov. 29, 2001

(86) PCT No.: PCT/BA01/00005

§ 371 (c)(1), (2), (4) Date: Sep. 10, 2004

(87) PCT Pub. No.: WO03/033017

PCT Pub. Date: Apr. 24, 2003

(65) Prior Publication Data

US 2005/0014696 A1 Jan. 20, 2005

(30) Foreign Application Priority Data

Oct. 18, 2001 (BA) .............................. BAP01898A

(51) Int. Cl.
*A61K 38/04* (2006.01)
(52) U.S. Cl. .................... 514/2; 514/14; 514/17
(58) Field of Classification Search .............. None
See application file for complete search history.

(56) References Cited

FOREIGN PATENT DOCUMENTS

WO WO 9909991 A1 * 3/1999
WO WO 0004873 A1 * 2/2000
WO WO 0069900 A2 * 11/2000

OTHER PUBLICATIONS (P. Konjecvoda, et al. J. Phys. Paris (2001) 95, pp. 277-281.*
P.W. Tinsley, et al. Peptides (1989) 9, pp. 1373-1379.*
P. Konjevoda,, et al. Croatica Chemica Acta. (2000) 73(4), pp. 1111-1120.*
Baranyi L.et al. (1995) "The antisense homology box: A new motif within proteins that encodes biologically active peptides." Nature Medicine 1: 894-901.
Blalock J.E. (1995) "Genetic Origins of protein shapes and interactions rules" Nature Medicine, 1: 876-878.
Konjevoda P. et al. (2000) "Protective Effects of Met-enkephalin on Alcohol Induced Gastric Lesions" Croat. Chem. Acta 73: 1111-1121.
Lipton J.M. et al. (1997) "Anti-inflammatory actions of the neuroimmunomodulator α-MSH" ImonoI. Today 18 (1997) 140-145.
Plotnikoff et al. (1997) "Methionine Enkephalin: A new Cytokine—Human Studies" Clin. Immunol. Immunnopath. 82: 93-101.
Štambuk N et al. (1999) "Computational Determination of biologically active motifs of the bone morphogenic protein precursors" Period. Biol. 101: 363-368.
Štambuk N. (1998) "On the Optimization of Complementary Protein Coding" in: S. Ohno, K. Aoki, M. Usui, E. Uchio (Eds.), Uveitis Today, Elsevier, Amsterdam, pp. 315-318.
Štambuck, et al. (1998) "Simple Three-step Method for the Analysis and Design of Repetitive and Bioactive protein Motifs", in: V. B. Bajić (Ed.), Advances in Systems Signals Control and Computers vol. II, IAAMSAD, and ANS, Durban, pp. 310-311.
Štambuk, N. et al. (1998) "Cytogenic effects on met-enkephalin (peptid-M) on human lymphocytes." Croat. Chem. Acta 71 591-605.

* cited by examiner

*Primary Examiner*—Andrew D Kosar
(74) *Attorney, Agent, or Firm*—Morgan, Lewis & Bockius LLP

(57) ABSTRACT

Repetitive and bioreactive regions of pro-opiliomelanocortin were identified using computational analysis. These regions KOMET, KOMET-1, KOMET-2, and KOMET-3 exhibit cytoprotective effects and may be administered to a patient to obtain better and stronger pharmacologic effects on the systemic and local modulation of inflammation and wound healing.

22 Claims, 1 Drawing Sheet

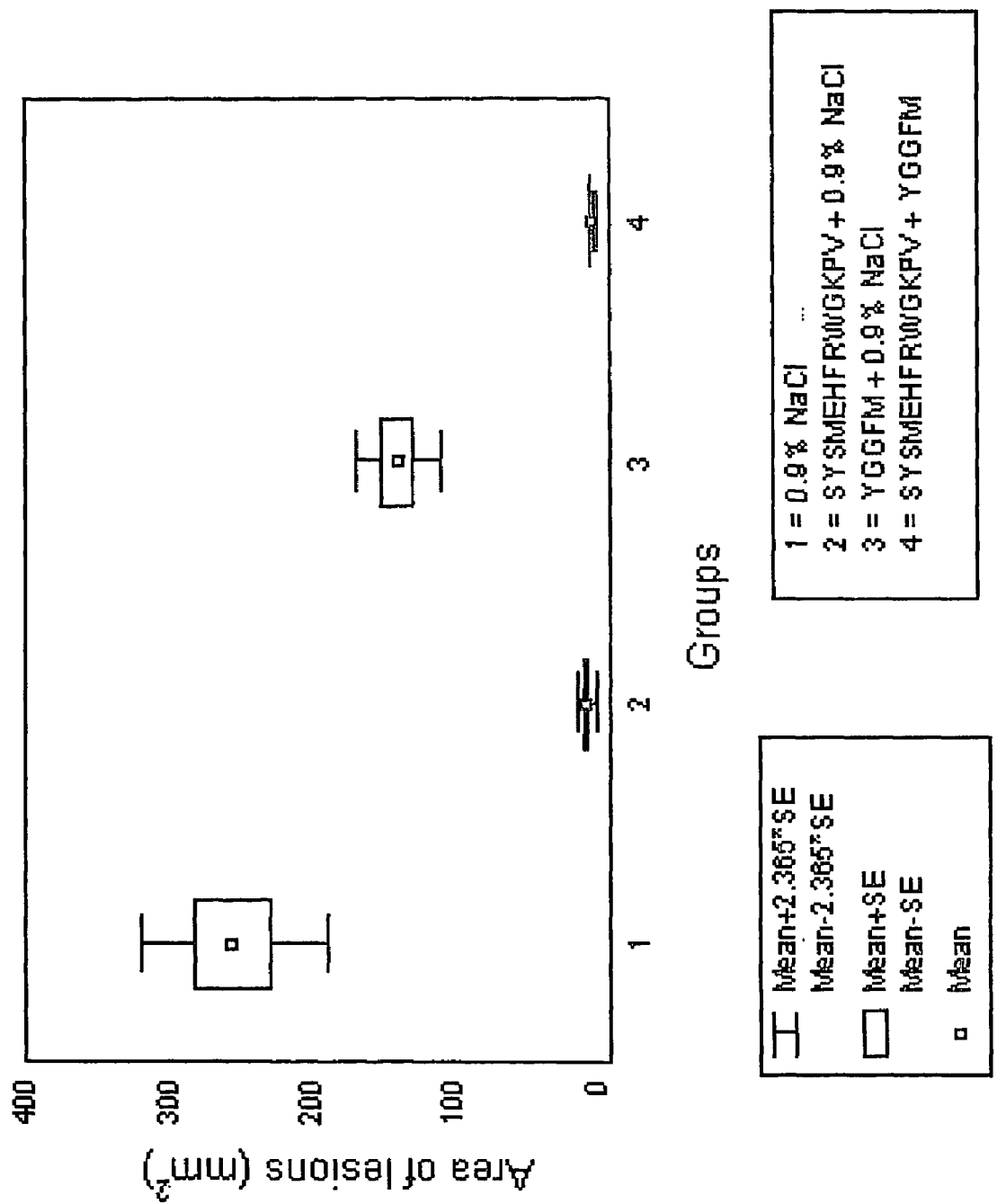

ADDITIVE CYTOPROTECTIVE EFFECTS OF TWO BIOACTIVE REGIONS OF PRO-OPIOMELANOCORTIN HORMONE

1) TECHNICAL AREA OF THE INVENTION

The invention is a combination of two bioactive peptides extracted from the pro-opiomelanocortin hormone that enables additive cytoprotective effects and modulation of the inflammatory response and tissue/wound healing. The combination of two pro-opiomelanocortin of peptides enables better pharmacologic effects and tissue lesion healing.

2) TECHNICAL PROBLEM

Bioactive parts of the protein and gene sequences are often 5 to 15 amino acids long and repetitive peptides, separated by larger amino acid blocks of undefined function (1-5). Computational analyses may be used for the extraction of such motifs and subsequent manipulation with the bioactive effects their protein regions (1-5). The invention represents a combination of two repetitive and bioactive regions of the pro-opiomelanocortin hormone that exhibits additive cytoprotective and pharmacological effects.

3) TECHNICAL DESCRIPTION

Repetitive peptide motifs within a single protein or a protein family represent, together with their matching complementary sequences, regions that are linked to the bioactivity of larger molecular structures (1-5).

Modern programming techniques, development of software and databases of the protein and gene structures enabled the computer modeling of repetitive, bioactive and complementary structures of a large number of different proteins (1-5). We analyzed repetitive and bioactive peptides of the pro-opiomelanocortin molecule by means of the software program SCAN (3-5).

4) PURPOSE OF THE INVENTION

The purpose of the invention is to obtain additive cytoprotective pharmacologic effects by combining two repetitive and bioactive peptides of the pro-opiomelanocortin hormone molecule.

Instead of the random pharmacologic screening of different pro-opiomelanocortin protein motifs, the software program SCAN was used to extract two repetitive and bioactive sequences (SYSMEHFRWGKPV (SEQ ID NO: 2) and YGGFM (SEQ ID NO: 1)). Two extracted sequences are present in the following molecules: pro-opiomelanocortin precursor, pro opiomelanocortin, corticotropin, melanotropin, lipotropin beta, proenkephalin, preproenkephalin, endorphin beta adrenorphin (see Table 1).

Bioactive peptide fragments SYSMEHFRWGKPV (SEQ ID NO: 2) and YGGFM (SEQ ID NO: 1) were tested individually and in combination, by means of the standard cytoprotection model of the 96% ethanol induced gastric lesions in male Wistar rats (6, 7). In the control group of 8 animals treated with physiological, saline the area of gastric lesions was $255.5 \pm 78.1$ mm$^2$ (mean ± standard deviation, FIG. 1) (7). In the group of 8 animals treated with the combination of peptides SYSMEHFRWGKPV (SEQ ID NO: 2) (1 mg/kg) and YGGFM (SEQ ID NO: 1) (10 mg/kg) the area of gastric lesions was $0.3 \pm 0.7$ mm$^2$ ($p<0.05$ compared to controls, FIG. 1) (7). In the group of 8 animals treated with peptide SYSMEHFRWGKPV (SEQ ID NO: 2) (1 mg/kg) the area of gastric lesions was $5.9 \pm 8$ mm$^2$ ($p<0.05$ compared to controls, FIG. 1) (7). In the group of 8 animals treated with peptide YGGFM (SEQ ID NO: 1) (10 mg/kg) the area of gastric lesions was $139.4 \pm 36.1$ mm$^2$ ($p<0.05$ compared to controls, FIG. 1). The combination of peptides SYSMEHFRWGKPV (SEQ ID NO: 2) and YGGFM (SEQ ID NO: 1) that provided best cytoprotective effect is patented under the name KOMET. Peptides or their combination did not show any irritation of the gastric mucosa (7).

5) FIGURES AND TABLES

Table 1 defines the combination of two bioactive sequences of pro-opiomelanocortin named KOMET, and three combinations of their chemical structural formulas KOMET-1, KOMET-2 and KOMET-3 (obtained by combining individual structural formulas).

FIG. 1 defines the cytoprotective effects of the bioactive peptide fragments SYSMEHFRWGKPV (SEQ ID NO: 2) and YGGFM (SEQ ID NO: 1) of the pro-opiomelanocortin molecule, and their combination KOMET, in the model of the ethanol induced gastric lesions in rats.

6) DESCRIPTION OF THE POSSIBLE APPLICATIONS OF THE INVENTION

Bioactive sequences KOMET, and the combination of their structural formulas formulas KOMET-1, KOMET-2 and KOMET-3 defined in Table 1 will be used as bioactive peptides for the modulation of the inflammation and wound healing. The purpose of defining structural formulas KOMET-1, KOMET-2 and KOMET-3 from the bioactive regions of pro-opiomelanocortin hormone (6-9) is to obtain structural formulas and/or sequences of the potential drugs in a quick and efficient way.

The aim of the invention KOMET, KOMET-1, KOMET-2 and KOMET-3 is to obtain a drug that prevents and stops tissue and organ damage in inflammatory and autoimmune diseases, as well as in trauma, infection and burns of the:

1. connective tissue, joints and bones;
2. central and peripheral nervous system, optic nerve, eye and ear;
3. skin, hair and nails;
4. digestive system, liver, pancreas, oral cavity, teeth and sinuses;
5. immune system, bone marrow lymph nodes and spleen;
6. cardiovascular system;
7. respiratory, system and respiratory mucosa; and
8. reproductive system.

6) INDUSTRIAL APPLICATIONS OF THE INVENTION

Bioactive sequences of the pro-opiomelanocortin KOMET, KOMET-1, KOMET-2, and KOMET-3 will be applied subcutaneously, intramuscularly, intraperitoneally and intravenously. Topical applications include ointments, creams, gels, suppositories, vaginal suppositories, eye-drops and ear-drops.

REFERENCES

1. L. Baranyi, W. Campbell, K. Ohishima et al., *Nature Medicine* 1 (1995) 894-901.
2. J. E. Blalock, *Nature Medicine,* 1(1995) 876-878.

3. N. Stambuk, *On the Optimization of Complementary Protein Coding*, in: S. Ohno, K. Aoki, M. Usui, E. Uchio (Eds.), *Uveitis Today*, Elsevier, Amsterdam, 1998, pp 315-318.
4. N. Stambuk and P. Konjevoda, *Period. Biol.* 101 (1999) 363-368.
5. N. Stambuk, N. Gotovac, M. Martinis et al. *Simple Three-step Method for the Analysis and Design of Repetitive and Bioactive protein Motifs*, in: V. B. Bajić (Ed.), Advances in Systems Signals Control and Computers vol. II, IAAM-SAD, and ANS, Durban, 1998, pp 310-311.
6. P. Konjevoda, N. Stambuk, D. Vikić-Topić et al. *Croat. Chem. Acta* 73 (2000) 1111-1121.
7. P. Konjevoda, N. Stambuk, G. Aralica and B. Pokrić, *J. Physiol.—Paris* 95 (1-6)(2001) 277-281.
8. J. M. Lipton and A. Catania, *Immunol. Today* 18 (1997) 140-145.
9. N. Stambuk N. Kopjar, K. Sentija, et al. *Croat. Chem. Acta* 71 (1998) 591-605.

TABLES AND FIGURES

Table 1. Combination of two bioactive and repetitive protein motifs (YGGFM (SEQ ID NO: 1) and SYSMEHFRWGKPV (SEQ ID NO: 2)) was determined computationally by means of the SCAN software (3-5) from the pro-opiomelanocortin precursor and pro-opiomelanocortin molecules. Repetitive peptide YGGFM is also present in the preproenkephalin, proenkephalin, lipotropin beta, endorphin beta and adrenorphin molecules (see (a) below). Peptide SYSMEHFRWGKPV (SEQ ID NO: 2) is additionally present in melanotropin and corticotropin molecules (see (b) below).

Combination of bioactive peptides YGGFM (SEQ ID NO: 1) and SYSMEHFRWGKPV (SEQ ID NO: 2) of the pro-opiomelanocortin molecule which are subject to the present invention is also known as KOMET.

Other combination of two sequences of both peptides are patented under the following names and structural formulas:

KOMET-1 characterized by the structural formula YGGFMSYSMEHFRWGKPVYGGFM (SEQ ID NO: 3), KOMET-2 characterized by the structural formula YGGFMSYSMEHFRWGKPV (SEQ ID NO: 4) and KOMET-3 characterized by the structural formula SYSMEHFRWGKPVYGGFM (SEQ ID NO: 5).

| (a) | | |
|---|---|---|
| No. | Sequence YGGFM | Residue |
| 1 | Adrenorphin | 1-5 |
| 2 | Endorphin beta | 1-5 |
| 3 | Preproenkephalin | 54-58, 61-65, 90-94, 140-144, 164-168, 215-219 |
| 4 | Proenkephalin | 100-104, 107-111, 136-140, 186-190, 210-214, 261-265 |
| 5 | Lipotropin beta | 59-63, 61-65 |
| 6 | Pro-opiomelanocortin precursor | 232-236 |
| 7 | Pro-opiomelanocortin | 3-7, 237-241 |

| (b) | | |
|---|---|---|
| No. | Sequence SYSMEHFRWGKPV | Residue |
| 1 | Melanotropin | 1-13 |
| 2 | Corticotropin | 1-13 |
| 3 | Pro-opiomelanocortin precursor | 133-145 |
| 4 | Pro-opiomelanocortin | 138-150 |

FIG. 1. FIG. 1 shows the cytoprotective effects of the bioactive peptide fragments SYSMEHFRWGKPV (SEQ ID NO: 2) and YGGFM (SEQ ID NO: 1) of the pro-opiomelanocortin molecule in a rat model of ethanol induced gastric lesion. Combination of the sequences KOMET (SYSMEHFRWGKPV (SEQ ID NO: 2)+YGGFM (SEQ ID NO: 1)) exhibits stronger cytoprotective effects than the individual sequences.

The invention claimed is:

1. A composition comprising two isolated peptides wherein the first isolated peptide consists of the amino acid sequence of SEQ ID NO: 1 and the second isolated peptide consists of the amino acid sequence of SEQ ID NO: 2, and wherein the composition is suitable for use in humans.

2. The composition of claim 1 wherein the composition is suitable for topical administration.

3. The composition of claim 2 wherein the composition is formulated as an ointment, cream, suppository, vaginal suppository, eye drop, ear drop or gel.

4. The composition of claim 1 wherein the composition is suitable for systemic administration.

5. The composition of claim 4 wherein the systemic administration is selected from the group consisting of subcutaneous, intramuscular, intraperitoneal and intravenous administration.

6. A method of reducing inflammation in a subject in need thereof comprising administering of two isolated peptides wherein the first isolated peptide consists of the amino acid sequence of SEQ ID NO: 1 and the second isolated peptide consists of the amino acid sequence of SEQ ID NO: 2.

7. A method of promoting wound healing in a subject in need thereof comprising administering of two isolated peptides wherein the first isolated peptide consists of the amino acid sequence of SEQ ID NO: 1 and the second isolated peptide consists of the amino acid sequence of SEQ ID NO: 2.

8. The method of claim 6 wherein the administration of the first and second polypeptide is sequential.

9. The method of claim 6 wherein the administration of the first and second polypeptide is simultaneous.

10. The method of claim 6 wherein the subject is human.

11. The composition of claim 1, wherein the composition reduces inflammation.

12. The composition of claim 1, wherein the composition promotes healing.

13. The composition of claim 1, wherein the composition does not contain SEQ ID NO: 3, 4 or 5.

14. A composition comprising two isolated peptides,
wherein the first isolated peptide contains the amino acid sequence of SEQ ID NO: 1 and consists of any amino acid sequence selected from the group consisting of SEQ ID NO: 1, 3 to 5,
wherein the second isolated peptide contains the amino acid sequence of SEQ ID NO: 2 and consists of any amino acid sequence selected from the group consisting of SEQ ID NO: 2 to 5, and
wherein the composition is suitable for use in humans.

15. The composition of claim 14, wherein the composition is suitable for topical administration.

16. The composition of claim 14, wherein the composition is formulated as an ointment, cream, suppository, vaginal suppository, eye drop, ear drop or gel.

17. The composition of claim 14, wherein the composition reduces inflammation.

18. The composition of claim 14, wherein the composition promotes healing.

19. The composition of claim 14, wherein the composition is suitable for systemic administration.

20. The composition of claim 19, wherein the systemic administration is selected from the group consisting of subcutaneous, intramuscular, intraperitoneal and intravenous administration.

21. A method of reducing inflammation in a subject in need thereof comprising administering a composition of claim 14.

22. A method of promoting wound healing in a subject in need thereof comprising administering a composition of claim 14.

* * * * *

SEQUENCE LISTING

<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Artificial amino acid sequence with a gap,
      numbered as a plurality (combination) of two separate sequences
      specified with separate sequence identifiers 1 and 2 (or vice
      versa). The combination (plurality) of sequence identifiers 1 and
      2 named KOMET enables better and stronger cytoprotective and
      pharmacologic effects than the ones obtained by means of the
      individual amino acid sequence identifiers.

<400> SEQUENCE: 1

Ser Tyr Ser Met Glu His Phe Arg Trp Gly Lys Pro Val
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Artificial amino acid sequence with a gap,
      numbered as a plurality (combination) of two separate sequences -continued specified with separate sequence identifiers 1 and 2 (or vice
versa). The combination (plurality) of sequence identifiers 1 and
2 named KOMET enables better and stronger cytoprotective and
pharmacologic effects than the ones obtained by means of the
individual amino acid sequence identifiers.

<400> SEQUENCE: 2

Tyr Gly Gly Phe Met
 1               5

<210> SEQ ID NO 3
<211> LENGTH: 23
<212> TYPE: PRT
<213> ORGANISM: Artificial Sequence
<220> FEATURE:
<223> OTHER INFORMATION: Designed amino acid sequence that is made up of
      two non-contiguous segments of a larger sequence or of segments
      from different sequences numbered as a separate sequence, with a
      separate sequence identifier (SEQ ID NO: 3). This artificial
      sequence is named KOMET-1.

<400> SEQUENCE: 3

Tyr Gly Gly Phe Met Ser Tyr Ser Met Glu His Phe Arg Trp Gly Lys
 1               5                  10                  15

Pro Val Tyr Gly Gly Phe Met
            20

<210> SEQ ID NO 4
<211> LENGTH: 18
<212> TYPE: PRT
<213> ORGANISM: Artificial Sequence
<220> FEATURE:
<223> OTHER INFORMATION: Designed amino acid sequence that is made up of
      two non-contiguous segments of a larger sequence or of segments
      from different sequences numbered as a separate sequence, with a
      separate sequence identifier (SEQ ID NO: 4). This artificial
      sequence is named KOMET-2.

<400> SEQUENCE: 4

Tyr Gly Gly Phe Met Ser Tyr Ser Met Glu His Phe Arg Trp Gly Lys
 1               5                  10                  15

Pro Val

<210> SEQ ID NO 5
<211> LENGTH: 18
<212> TYPE: PRT
<213> ORGANISM: Artificial Sequence
<220> FEATURE:
<223> OTHER INFORMATION: Designed amino acid sequence that is made up of
      two non-contiguous segments of a larger sequence or of segments
      from different sequences numbered as a separate sequence, with a
      separate sequence identifier (SEQ ID NO: 5). This artificial
      sequence is named KOMET-3.

<400> SEQUENCE: 5

Ser Tyr Ser Met Glu His Phe Arg Trp Gly Lys Pro Val Tyr Gly Gly
 1               5                  10                  15

Phe Met